United States Patent [19]

Takasugi et al.

[11] 4,392,491
[45] Jul. 12, 1983

[54] INJECTOR

[75] Inventors: Mitsuo Takasugi, Yokohama; Ajoshio Okuyama, Tokyo, both of Japan

[73] Assignee: Colpo Company Limited, Tokyo, Japan

[21] Appl. No.: 288,198

[22] Filed: Jul. 29, 1981

[30] Foreign Application Priority Data

Aug. 5, 1980 [JP] Japan .................. 55-106806

[51] Int. Cl.³ ............................ A61M 5/00
[52] U.S. Cl. .................... 604/202; 604/234; 604/900
[58] Field of Search ........... 128/218 D, 218 DA, 215, 128/220, 221, 218 P, 218 PA

[56] References Cited

U.S. PATENT DOCUMENTS 2,950,717  8/1960  Bouet .......................... 128/218 D

FOREIGN PATENT DOCUMENTS 1069835  7/1956  Fed. Rep. of Germany ... 128/218 D
1205021  9/1970  United Kingdom ........ 128/218 DA Primary Examiner—John D. Yasko
Attorney, Agent, or Firm—Browdy & Neimark

[57] ABSTRACT

This invention relates to an injector with a cartridge for a liquid medicine, which is suitable as a throwaway type or a re-use type, and especially displays remarkable effects at urgent occasions. This injector substantially comprises an injector tube housing a cartridge into a body thereof and a cylinder slidably supporting a piston such that it is not removed therefrom at its end portion and in the injector tube by its front half part. Further, the cartridge is equipped with a concave on its bottom and the piston is equipped with a convex on its head for engaging means. The needle portion comprises an injecting needle and a hollow needle inwardly extending from the needle. If the needle portion is urged while it is fitted to the injector tube, the hollow needle pierces the cartridge and reaches the liquid medicine in the cartridge. The cylinder is defined with a stopper at its circumferential edge to restrain the piston with respect to the cylinder. On use, the piston goes at its head into the cartridge from its bottom and makes a double film of the cartridge by turning it over so that the double film is positioned between the head of the piston and the inner wall of the injector tube, whereby all of the liquid in the cartridge is supplied into the injecting needle.

5 Claims, 3 Drawing Figures

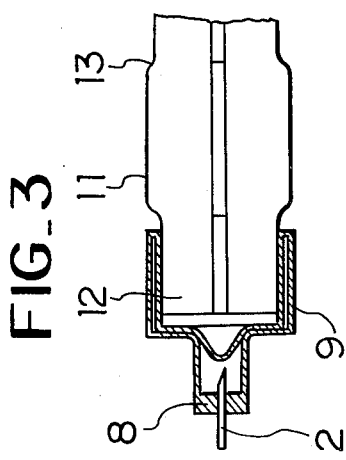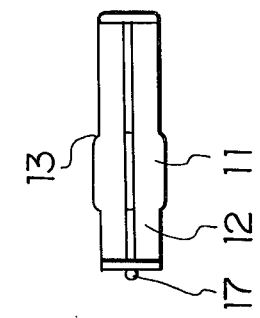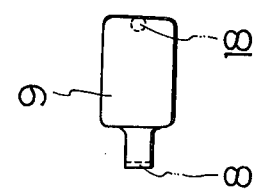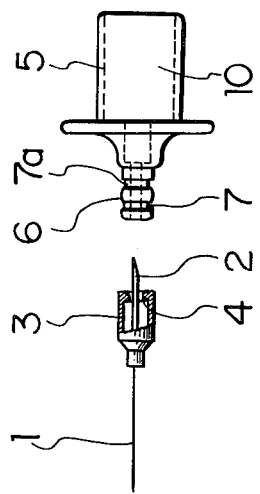

INJECTOR

BACKGROUND OF THE INVENTION

1. Field of the Invention

An instant injector may be, after use, thrown away or re-used, and even at emergency it may be rapidly charged with a liquid medicine containing cartridge.

2. Description of the Prior Art

There have already been proposed such urgent case's injectors that an injector body as a tube has been in advance filled with injecting liquid, and a mouth is tight-sealed with a temporary cover pierced with a needle. Such an injector is also known that an injector tube is integrally composed with an injecting needle and is prior filled with the medicine liquid and the needle is sealed on its end point. Since a squeezing tube is pressed by the operator with his fingers, it would be deformed and could not always inject a determined amount of the liquid, and it would take a fairly long time. For the medicine liquid contained in the injector, precision is required to sliding between a cylinder and a piston, otherwise the liquid will leak and a piston stopper should be provided.

SUMMARY OF THE INVENTION

An object of the invention is to provide a cartridge type injector which could be operated rapidly and exactly even at the urgent occasions.

Another object of the invention is to provide a cartridge type injector which is possible to do a vascular injection.

A further object of the invention is to provide an injector which may be re-used only by exchanging the cartridge without disinfection each time.

A still further object of the invention is to provide an injector which could inject almost 100% the medicine contained in the charged cartridge.

Another object of the invention is to provide an injector which never misses a piston.

Other and further objects, features and advantages of the invention will appear more fully from the following description.

BRIEF DESCRIPTION OF THE DRAWING

FIG. 1 is a vertical cross sectional view of the most preferred embodiment of the invention, FIG. 2 is a view showing disassembly of the above mentioned embodiment, and FIG. 3 is an enlarged vertical cross sectional view showing an operation of the embodiment.

DETAILED DESCRIPTION OF THE INVENTION

As shown, the present invention is substantially composed of a needle portion, an injector tube, a cylinder and a piston. The needle portion has a hollow needle 2 of a desired length extending in opposition to the injecting needle 1, and is provided in ring with a projection 4 within a fitting portion 3 to be engaged with a needle connecting portion 6 of an injecting tube 5. The injecting tube 5 is defined with more than one of concaves 7 and 7a on the connecting portion 6, and is formed with a hollow space 10 to be charged with a film-like cartridge 9 with a sealing cover 8 holding the liquid as shown in FIG. 2. With respect to the injecting needle, the projection 4 engages the concave 7 into restraint, and accordingly the hollow needle 2 is positioned to have its end portion slightly spaced from the sealing cover 8. The piston 11 has an engaging convex 17 on a head 12 thereof, and it makes the head 12 narrower in diameter than an inner diameter of the space 10 over more than ½ of the depth of the space 10, and forms a step 13 on a sliding surface following the head 12. The position of the step 13 is restrained at a reduced diameter end opening which defines a stop 15 of a cylinder 14. The cylinder 14 includes a large diameter portion and a small diameter portion. The large diameter portion of cylinder 15 is adapted to be coaxially positioned about the body of the injecting tube 5, and the piston 11 is inserted into the small diameter portion of cylinder 14 from the large diameter portion of cylinder. The small diameter portion has the stop 15 at a circumferential edge of an opening thereof, so that the piston 11 contacts, when moving in opposition, to the step 13 and does not get out from the cylinder 14.

The injector tube 5 is air-tightly mounted with a needle protecting cap 16 on a neck thereof. The cartridge 9 has an engaging concave 18 in correspondence to the engaging convex 17 of the piston 11. The positioning relation of the convex 17 and the concave 18 may be reversed, that is, it is allowable to make a projection on the bottom of the cartridge 9 and makes a recess on the head of the piston 11.

The injector of this invention is constructed as mentioned above, and is set up by positioning the cartridge 9 into the hollow interior 10 of the injector tube 5 having the injecting needle, and inserting and pushing the piston 11 into the cylinder 14 from its large diameter portion until the step 13 contacts the stop 15. Then, the large diameter portion of the cylinder 14 is positioned coaxially of and radially outwardly of the injector tube 5, and the piston 11 pushed slightly so that the convex 17 is engaged with the concave 18 and thus the assembly of the injector is completed (refer to FIG. 1). For performing the injection, the cap 16 is removed and the pressure is effected to the injecting needle 1 toward the tube 5, so that the projection 4 is urged into the other groove 7a from the groove 7, whereby the hollow needle 2 pierces the sealing cover 8 of the cartridge 9 and reaches the liquid agent therein. Then, when pushing the piston 11 on its end portion, the liquid agent in the cartridge 9 goes to the injecting needle 1 through the hollow needle 2. As the piston head 12 is pushing the bottom of the cartridge 9 while the convex 17 is engaged with the concave 18, the cartridge film overlaps by turning over itself (doubles over) and makes a double film, and the liquid agent in the cartridge 9 exhausts all the amount up to its throat. This amount is a predetermined amount. If the piston 11 is moved back just after the injection and since the engagement between the convex 17 and the concave 18 is maintained, the bottom of the cartridge 9 is pulled by the piston 11. Therefore, it is permitted to move back the piston and it is possible to confirm whether the injection is properly made in the blood vessel.

The present invention makes, by one action of fitting the needle, a connection of the liquid agent in the cartridge and the hollow needle and further the injecting needle. Therefore, it is like that the needle goes into Ampulle, and the liquid never touches other members. This is very hygienic and being without disinfection and possible to use it only by charging the cartridge, this is very suitable the urgent occasions in the outdoors, and further the liquid does not leak at all. The invention is much suited to the urgent cases, since it may omit time and steps for conventionally breaking Ampulle at its neck, absorbing the liquid into the injector, expelling the air from the tube and injecting the liquid. The invention does not need to pay attention to the precision of the air-tight sliding between the cylinder and the piston or to the air tight packing of the piston head, and no precision is required to any parts. Also in the instant injector, transparency is preferable, but opacity for heat and light insulation in view of the weather resistibility of the liquid is not impreferable, and it is sufficient to make a mark for the liquid volume at the end of the piston. The cartridge is pushed by the piston and the cartridge film is turned over (doubled over) between the injector tube and the piston head. This condition corresponds to the slide contacting surface between the cylinder and the piston, so that the liquid is all exhausted. Thus, the invention is very useful to calamities such as earthquakes, mountain-climbing, travelling, fire accidents and others. This invention is an excellent injector in safety, stability and function.

What is claimed is:

1. An injector comprising an injection needle means, an injector tube comprising a neck portion and a hollow body portion open at the end thereof opposite said neck portion, said needle means being detachably secured to said neck portion of said injector tube, said hollow body portion of said injector tube being adapted to receive a cartridge on the interior of said body portion, a cylinder having a cylinder body portion coaxially positioned about said hollow body portion of said injector tube, the opposite end of said cylinder having a reduced diameter opening defining a stop, a piston having a piston head engageable with the bottom of the cartridge, said piston being insertable in said cylinder at an end of said cylinder spaced from said opposite end of said cylinder, said piston having a stepped diameter which is restrained by said stop whereby to limit the movement of said piston when said stepped diameter of said piston engages said stop.

2. An injector comprising an injector tube adapted to receive a cartridge on the interior thereof, a cylinder including a first cylinder body portion receiving said injector tube therein, said cylinder including a second cylinder body portion contiguous and communicating with said first body portion, a piston including a piston head normally positioned substantially within said second body portion but movable into said injector tube while exerting pressure against the facing bottom end of a cartridge positioned in said injector tube, the diameter of said piston head being sufficiently less than the internal diameter of said injector tube whereby to provide space radially between said piston head and said internal diameter of said injector tube over the range of axial travel of said piston head whereby to permit the wall of said cartridge to be doubled over in a direction axially of said cartridge and of said injector tube due to the pressure exerted by said piston on said bottom end of said cartridge.

3. An injector as defined in claim 2 in which said cartridge and said piston head define two cooperating members, one of said members having a protuberance thereon in facing relation to the other of said members, said other member having a recess therein which is engaged by said protuberance of said one member, whereby to engage said piston head with said cartridge.

4. An injector as defined in claim 2 in which said injector tube includes a tube portion for connection to an injection needle means, said tube portion including a first groove and a second groove in spaced relation from each other on said tube portion, a fitting portion in supporting relation to said injection needle means, said fitting portion being initially engageable with said first groove means to maintain said needle means in spaced relation to said cartridge, said fitting means being engageable with said second groove when said injector is being used for performing an injection, whereby to position said needle means in communication with the contents of said cartridge.

5. An injector as defined in claim 2 in which said piston is provided with an enlarged diameter portion intermediate the length thereof and said cylinder is provided with an open end of smaller diameter than said enlarged diameter portion of said piston, whereby to retain at least a predetermined portion of the length of said piston in said cylinder.

* * * * *